United States Patent
Boudon et al.

(10) Patent No.: US 10,179,797 B2
(45) Date of Patent: Jan. 15, 2019

(54) PHOSPHINIC PEPTIDE DERIVATIVES FOR USE AS MMP-12 INHIBITORS

(71) Applicant: DSM IP ASSETS B.V., Heerlen (NL)

(72) Inventors: Stéphanie Boudon, Kaiseraugst (CH); Eileen Jackson, Kaiseraugst (CH); Rolf Schuetz, Kaiseraugst (CH); Jürgen Herbert Vollhardt, Kaiseraugst (CH); Peter Wikstroem, Kaiseraugst (CH); Eliane Ursula Wandeler, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/774,649

(22) PCT Filed: Nov. 23, 2016

(86) PCT No.: PCT/EP2016/078511
§ 371 (c)(1),
(2) Date: May 9, 2018

(87) PCT Pub. No.: WO2017/093093
PCT Pub. Date: Jun. 8, 2017

(65) Prior Publication Data
US 2018/0319829 A1    Nov. 8, 2018

(30) Foreign Application Priority Data

Nov. 30, 2015 (EP) .................................. 15197009

(51) Int. Cl.
| | | |
|---|---|---|
| *A61Q 19/08* | (2006.01) | |
| *A61Q 19/00* | (2006.01) | |
| *A61K 31/675* | (2006.01) | |
| *A61K 31/662* | (2006.01) | |
| *A61K 31/67* | (2006.01) | |
| *C07C 53/18* | (2006.01) | |
| *A61K 8/55* | (2006.01) | |
| *C07F 9/6553* | (2006.01) | |
| *C07F 9/30* | (2006.01) | |
| *C07F 9/572* | (2006.01) | |

(52) U.S. Cl.
CPC .......... *C07F 9/655354* (2013.01); *A61K 8/55* (2013.01); *A61K 31/662* (2013.01); *A61K 31/67* (2013.01); *A61K 31/675* (2013.01); *A61Q 19/00* (2013.01); *A61Q 19/08* (2013.01); *C07C 53/18* (2013.01); *C07F 9/306* (2013.01); *C07F 9/5728* (2013.01)

(58) Field of Classification Search
CPC ...... A61Q 19/08; A61Q 19/00; A61K 31/675; A61K 31/662; A61K 31/67; A61K 8/55; C07C 53/18
See application file for complete search history.

(56) References Cited

PUBLICATIONS

Chen et al., 2003, caplus an 2003:509539.*
Raguin et al., 2005, Angewandte Chemie International Edition, 44, 4058-4061.*
Schreiter et al., 2012, caplus an 2012:1843490.*
International Search Report for PCT/EP2016/078511, dated Jan. 12, 2017, 4 pages.
Written Opinion of the ISA for PCT/EP2016/078511, dated Jan. 12, 2017, 6 pages.
Schiodt, et al. "Phosphinic Peptide Inhibitors of Macrophage Metalloelastase (MMP-12). Selectivity and Mechanism of Binding.", Chemical Abstracts Service, Columbus, Ohio, US, 2001 XP002756234, 34 pages.
Schiodt, et al. "Phosphinic Peptide Inhibitors of Macrophage Metalloelastase (MMP-12). Selectivity and Mechanism of Binding", Current Medicinal Chemistry, vol. 8, No. 8, 2016, XP008179667, 10 pages.

* cited by examiner

*Primary Examiner* — Sun Jae Yoo
(74) *Attorney, Agent, or Firm* — Nixon & Vanderhye P.C.

(57) ABSTRACT

This invention relates to compounds that are selective inhibitors of Matrix Metalloprotease-12 (MMP-12), to cosmetic and pharmaceutical compositions containing them, and to their use in the prevention and/or treatment of ailments associated with MMP-12. Formula (I).

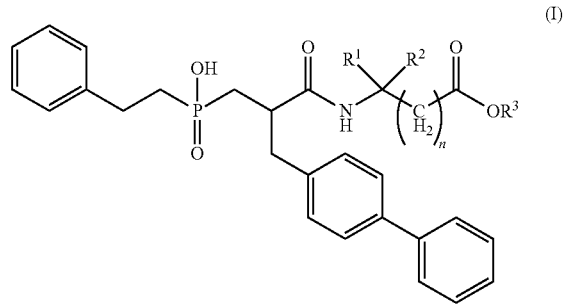

11 Claims, No Drawings

PHOSPHINIC PEPTIDE DERIVATIVES FOR USE AS MMP-12 INHIBITORS

This application is the U.S. national phase of International Application No. PCT/EP2016/078511 filed Nov. 23, 2016, which designated the U.S. and claims priority to EP Patent Application No. 15197009.2 filed Nov. 30, 2015, the entire contents of each of which are hereby incorporated by reference.

This invention relates to compounds that are selective inhibitors of Matrix Metalloprotease-12 (MMP-12), to cosmetic and pharmaceutical compositions containing them, and to their use in the prevention and/or treatment of ailments associated with MMP-12.

A major characteristic of aged and prematurely aged skin is a high degree of fragmentation of the dermal matrix wherein MMPs are known to play a major role in protein degradation such as the degradation of elastin and collagen, which in turn affects the structural integrity of the dermis. Thus, protection of extracellular matrix proteins such as elastin and collagen in aged or photo aged human skin by reduction of MMPs is vital to retard the clinical manifestations of skin aging such as wrinkles, sagging, and laxity.

In this regard it is well documented in human clinical trials that retinol treatment reduces matrix metalloprotease expression and stimulates collagen as well as elastin synthesis in naturally aged, sun protected but also in photodamaged skin via an inhibitory effect inter alia on MMP-12. Retinol, however, is known to have serious side effects such as skin irritation. Furthermore, retinol is not very stable in cosmetic compositions and thus not easy to formulate.

Thus, there is an ongoing need for novel MMP-12 inhibitors which are potentially useful in the treatment of age-associated impairments in dermal integrity and thus delaying the onset of ageing.

Surprisingly it has been found that specific novel compounds of formula (I)

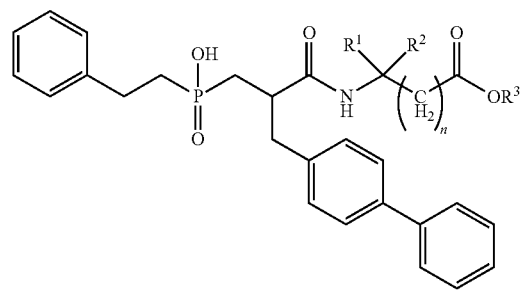

wherein
n is 0, 1 or 2,
$R^1$ is H, or an amino acid side chain which, if a functional group is present, may optionally be substituted by a $C_1$-$C_6$alkyl group, a $C_1$-$C_6$alkylcarbonyl group or a $C_1$-$C_6$alkoxycarbonyl group,
$R^2$ is H or Methyl and
$R^3$ is selected from the group consisting of H, a $C_1$-$C_6$alkyl group and an aryl$C_1$-$C_6$alkanyl group.
are highly effective MMP-12 inhibitors at very low use levels. Furthermore, they are stable upon formulation in cosmetic compositions and thus particularly suitable for the treatment of age-associated impairments in dermal integrity.

Thus, in a first aspect, the present invention relates to a compound of formula (I)

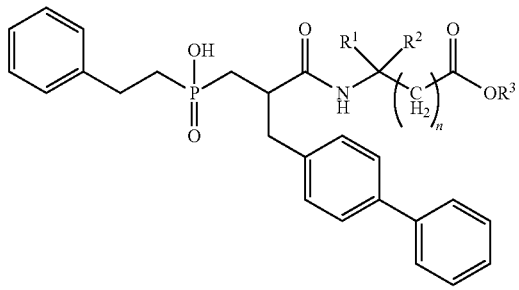

wherein
n is 0, 1 or 2,
$R^1$ is H, or an amino acid side chain which, if a functional group is present, may optionally be substituted by a $C_1$-$C_6$alkyl group, a $C_1$-$C_6$alkylcarbonyl group or a $C_1$-$C_6$alkoxycarbonyl group,
$R^2$ is H or Methyl, and
$R^3$ is selected from the group consisting of H, a $C_1$-$C_6$alkyl group and an aryl$C_1$-$C_6$alkanyl group
or a cosmetically acceptable salt thereof.

The term "side chain" of an amino acid refers to that portion of the amino acid attached to the common $NH_2$—$\overset{|}{C}H$—COOH backbone of the respective amino acids. For instance, the side chain of serine is —$CH_2$—OH and the side chain of alanine is —$CH_3$.

The term "amino acid" as used herein refers to any natural or unnatural amino acid.

The term 'natural amino acid' refers to the 20 proteogenic (protein-forming) amino acids coded in the genetic code. These are: alanine, leucine, isleucine, valine, methionine, cysteine, serine, threonine, aspartic acid, asparagine, glutamic acid, glutamine, arginine, lysine, tryptophan, histidine, phenyl alanine, tyrosine, glycine and proline. Unnatural amino acids refers any organic compounds containing amine (—$NH_2$) and carboxylic (—COOH) functional group. Particular preferred in all embodiments of the present invention are amino acids of the general formula $H_2NCR^1R^2COOH$, beta amino acids of general formula $H_2NCR^1 R^2CH_2COOH$, and gamma aminoacids of general formula $H_2NCR^1R^2CH_2CH_2COOH$, wherein $R^1$ and $R^2$ are as defined above.

The term 'substituted' as used herein refers to the substitution of a functional group present in the side chain of the respective amino such as an —OH, —$NH_2$ or —NH— group acid.

Examples of $C_1$-$C_6$alkyl groups are unbranched $C_1$-$C_6$alkyl or branched $C_3$-$C_6$alkyl groups such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl groups. Preferred $C_1$-$C_6$alkyl groups are methyl, ethyl and 1,1-dimethylethyl. In a most preferred embodiment $R^3$ is selected from the group consisting of H, methyl and 1,1-dimethylethyl (=tert-butyl).

Examples of arylC$_1$-C$_6$alkanyl groups include, but are not limited to benzyl groups. The most preferred arylC$_1$-C$_6$alkanyl group in all embodiments of the present invention is the benzyl group.

It is well understood, that the present invention encompasses the compounds of formula (I) as optically pure isomers such as e.g. as pure enantiomers or stereoisomers as well as mixtures of different isomers such as e.g. as racemates, or mixtures of diastereoisonmers.

The term 'or a cosmetically acceptable salt thereof refers to compounds of formula (I) in the form of acid and addition salt such as in the form of a chloride, an acetate or a trifluoroacetate salt or a salt formed by the addition of a base such as an alkali or earth alkaline salt, in particular lithium, sodium, potassium, magnesium or calcium salts. Most preferred according to the present invention are the compounds as such or in the form of their addition salt with acetic acid or trifluoroacetic acid. Most preferred are the compounds as such or in the form of their addition salt with trifluoroacetic acid. Such salts are easily prepared by a person skilled in the art.

Preferred amino acid side chains are the nonpolar or uncharged polar side chains of amino acids such as in particular the side chains of asparagine, glutamine, phenylalanine, methionine, valine, glycine, 2,4-diaminobutyric acid, 2-aminobutyric acid, alanine, leucine, isoleucine, norleucine, tryptophan, thiotryptophan, cyclohexylglycine, α-amino-2-naphthalenepropionic acid, serine, threonine, tyrosine, proline as well as cysteine.

Particular advantageous unsubstituted amino acid side chains in all embodiments of the present invention are the ones of phenylalanine, methionine, valine, thiotryptophan, isoleucine, tryptophan, 2,4-diaminobutyric acid, leucine, α-amino-2-naphthalenepropionic acid, norleucine, asparagine, alanine, 2-amino butyric acid, and cyclohexylglycine, most preferred are the ones of thiotryptophan, isoleucine, tryptophan, 2,4-diaminobutyric acid, leucine, α-amino-2-naphthalenepropionic acid, norleucine, asparagine, alanine, 2-amino butyric acid, and cyclohexylglycine.

If present, the functional groups of the amino acid side chain are preferably either unsubstituted or substituted with a C$_1$-C$_6$alkoxycarbonyl group, such as most preferably with a tert-Butyloxycarbonyl (Boc) group. Most preferred substituted amino acid side chains according to the invention are the side chains of 2-amino-4-(tert-butoxycarbonylamino)butyric acid and 1-[(1,1-dimethylethoxy)carbonyl]-tryptophan.

Particular advantageous compounds of formula (I) are the ones
wherein
n is 0, 1 or 2, preferably 0 or 2,
R$^1$ is H or an amino acid side chain of thiotryptophan, isoleucine, tryptophan, 2,4-diaminobutyric acid, leucine, α-amino-2-naphthalenepropionic acid, norleucine, asparagine, alanine, 2-amino butyric acidcyclohexylglycine, 2-amino-4-(tert-butoxycarbonylamino) butyric acid and 1-[(1,1-dimethylethoxy)carbonyl]-tryptophan
R$^2$ is H or methyl, preferably H, and
R is selected from the group consisting of H, a methyl group, a tert.-butyl group and a benzyl group.

Even more advantageous compounds of formula (I) are the ones
wherein
n is 0 or 2,
R$^1$ is H or an amino acid side chain of thiotryptophan, isoleucine, tryptophan, 2,4-diaminobutyric acid, leucine, α-amino-2-naphthalenepropionic acid, norleucine, asparagine, alanine, 2-amino butyric acid, cyclohexylglycine, 2-amino-4-(tert-butoxycarbonylamino) butyric acid and 1-[(1,1-dimethylethoxy)carbonyl]-tryptophan
R$^2$ is H and
R$^3$ is selected from the group consisting of H, a methyl group, a tert.-butyl group and a benzyl group.

Most preferred compounds of formula (I) are outlined in table 1:

TABLE 1

| Structure | Name |
|---|---|
| (structure shown with n = 0, R$^1$ = thiotryptophan side chain, R$^2$ = H, R$^3$ = CH$_3$) | (I)-a (2-([1,1'-biphenyl]-4-ylmethyl)-3-((3-(benzo[b]thiophen-3-yl)-1-methoxy-1-oxopropan-2-yl)amino)-3-oxopropyl)(phenethyl)phosphinic acid |

TABLE 1-continued

| Structure | Name |
|---|---|
| 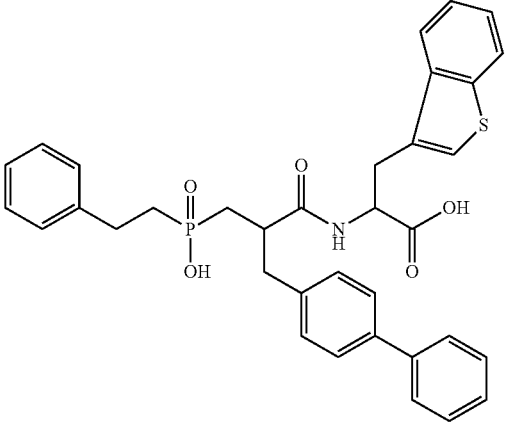 [SMILES: O=C(NC(Cc1csc2ccccc12)C(=O)O)C(Cc1ccc(-c2ccccc2)cc1)CP(=O)(O)CCc1ccccc1]<br>n = 0<br>R¹ = thiotryptophan side chain<br>R² = H<br>R³ = H | (I)-b  2-(3-([1,1'-biphenyl]-4-yl)-2-((hydroxy(phenethyl)phosphoryl)methyl)propanamido)-3-(benzo[b]thiophen-3-yl)propanoic acid |
| 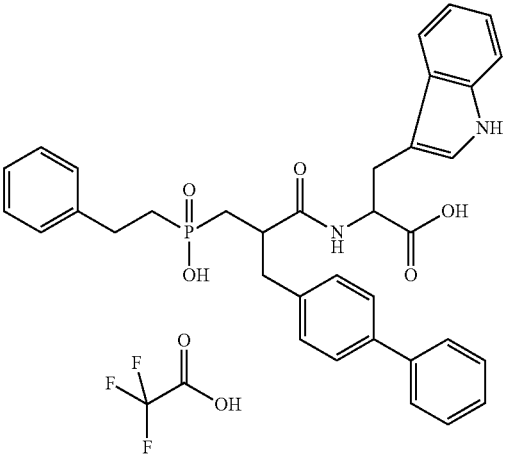 [SMILES: O=C(NC(Cc1c[nH]c2ccccc12)C(=O)O)C(Cc1ccc(-c2ccccc2)cc1)CP(=O)(O)CCc1ccccc1 ; O=C(O)C(F)(F)F]<br>n = 0<br>R¹ = thiotryptophan side chain<br>R² = H<br>R³ = H | (I)-c  (3-([1,1'-biphenyl]-4-yl)-2-((hydroxy(phenethyl)phosphoryl)methyl)propanoyl)tryptophan compound with 2,2,2-trifluoroacetic acid (1:1) |
| 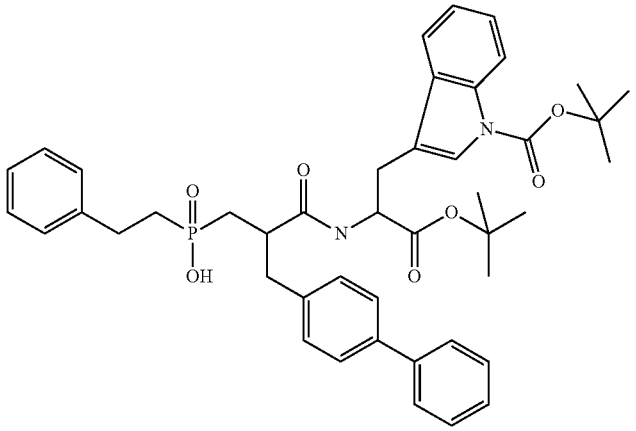 [SMILES: CC(C)(C)OC(=O)C(Cc1cn(C(=O)OC(C)(C)C)c2ccccc12)NC(=O)C(Cc1ccc(-c2ccccc2)cc1)CP(=O)(O)CCc1ccccc1]<br>n = 0<br>R¹ = N-Boc substituted tryptophan side chain<br>R² = H<br>R³ = CH(CH₃)₃ | (I)-d  (2-([1,1'-biphenyl]-4-ylmethyl)-3-((1-(tert-butoxy)-3-(1-(tert-butoxycarbonyl)-1H-indol-3-yl)-1-oxopropan-2-yl)amino)-3-oxopropyl)(phenethyl)phosphinic acid |

TABLE 1-continued

| Structure | Name |
|---|---|
| 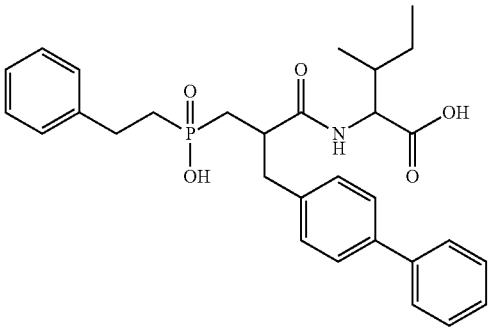 [SMILES: CCC(C)C(NC(=O)C(Cc1ccc(-c2ccccc2)cc1)CP(=O)(O)CCc1ccccc1)C(=O)O]<br>n = 0<br>R¹ = isoleucine side chain<br>R² = H<br>R³ = H | (I)-e 2-(3-([1,1'-biphenyl]-4-yl)-2-((hydroxy(phenethyl)phosphoryl)methyl)propanamido)-3-methylpentanoic acid |
| 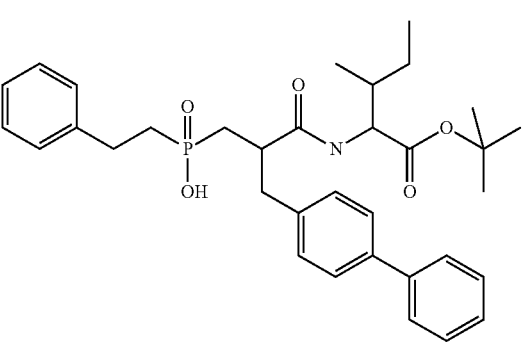 [SMILES: CCC(C)C(NC(=O)C(Cc1ccc(-c2ccccc2)cc1)CP(=O)(O)CCc1ccccc1)C(=O)OC(C)(C)C]<br>n = 0<br>R¹ = isoleucine side chain<br>R² = H<br>R³ = CH(CH$_3$)$_3$ | (I)-f (2-([1,1'-biphenyl]-4-ylmethyl)-3-((1-(tert-butoxy)-3-methyl-1-oxopentan-2-yl)amino)-3-oxopropyl)(phenethyl)phosphinic acid |
| 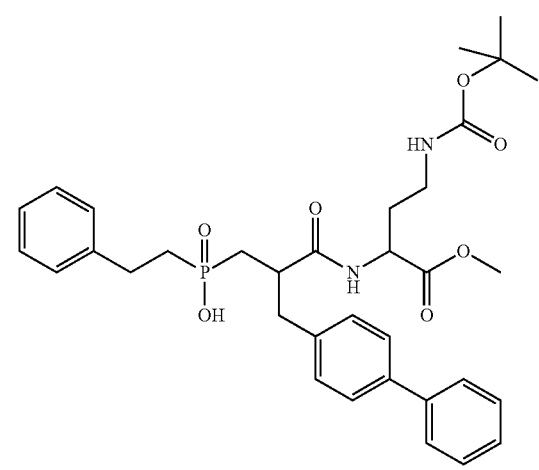 [SMILES: COC(=O)C(CCNC(=O)OC(C)(C)C)NC(=O)C(Cc1ccc(-c2ccccc2)cc1)CP(=O)(O)CCc1ccccc1]<br>n = 0<br>R¹ = Boc substituted 2,4-diaminobutryic acid side chain<br>R² = H<br>R³ = CH$_3$ | (I)-g (2-([1,1'-biphenyl]-4-ylmethyl)-3-((4-((tert-butoxycarbonyl)amino)-1-methoxy-1-oxobutan-2-yl)amino)-3-oxopropyl)(phenethyl)phosphinic acid |

TABLE 1-continued

| Structure | Name |
|---|---|
| n = 0<br>R¹ = leucine side chain<br>R² = H<br>R³ = CH(CH₃)₃ | (I)-h (2-([1,1'-biphenyl]-4-ylmethyl)-3-((1-(tert-butoxy)-4-methyl-1-oxopentan-2-yl)amino)-3-oxopropyl)(phenethyl)phosphinic acid |
| n = 0<br>R¹ = α-amino-2-naphthalenepropionic acid side chain<br>R² = H<br>R³ = H | (I)-i 2-(3-([1,1'-biphenyl]-4-yl)-2-((hydroxy(phenethyl)phosphoryl)methyl)propanamido)-3-(naphthalen-2-yl)propanoic acid |
| n = 0<br>R¹ = norleudine side chain<br>R² = H<br>R³ = CH₃ | (I)-j (2-([1,1'-biphenyl]-4-ylmethyl)-3-((1-methoxy-1-oxohexan-2-yl)amino)-3-oxopropyl)(phenethyl)phosphinic acid |
| n = 0<br>R¹ = norleucine side chain<br>R² = H<br>R³ = H | (I)-k 2-(3-([1,1'-biphenyl]-4-yl)-2-((hydroxy(phenethyl)phosphoryl)methyl)propanamido)hexanoic acid |

TABLE 1-continued

| Structure | | Name |
|---|---|---|
| 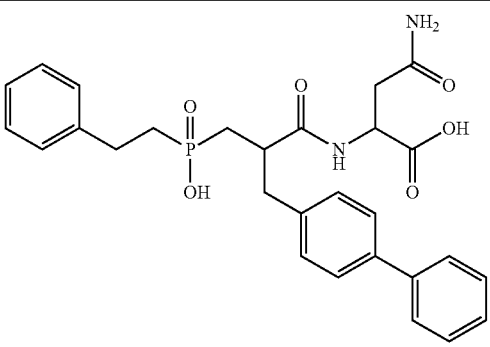<br>n = 0<br>R¹ = asparagine side chain<br>R² = H<br>R³ = H | (I)-l | (3-([1,1'-biphenyl]-4-yl)-2-((hydroxy(phenethyl)phosphoryl)methyl)propanoyl)asparagine |
| 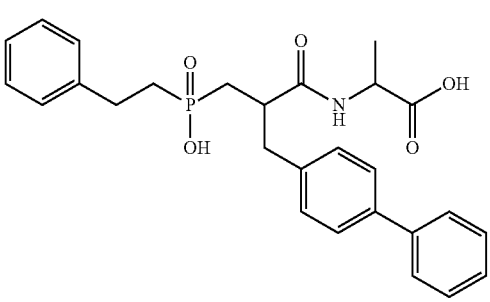 [SMILES: CC(NC(=O)C(Cc1ccc(-c2ccccc2)cc1)CP(=O)(O)CCc1ccccc1)C(=O)O]<br>n = 0<br>R¹ = alanine side chain<br>R² = H<br>R³ = H | (I)-m | (3-([1,1'-biphenyl]-4-yl)-2-((hydroxy(phenethyl)phosphoryl)methyl)propanoyl)alanine |
| 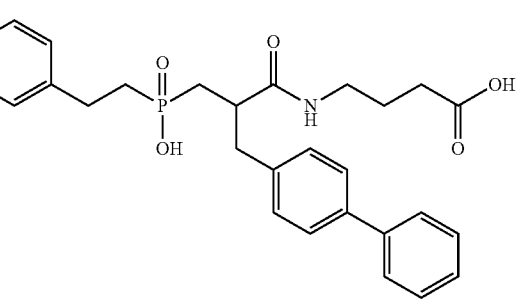<br>n = 2<br>R¹ = H<br>R² = H<br>R³ = H | (I)-n | 4-(3-([1,1'-biphenyl]-4-yl)-2-((hydroxy(phenethyl)phosphoryl)methyl)propanamido)butyric acid |
| 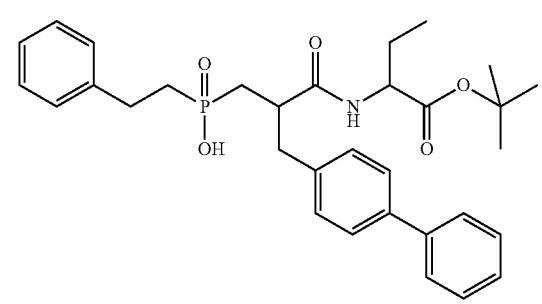 [SMILES: CCC(NC(=O)C(Cc1ccc(-c2ccccc2)cc1)CP(=O)(O)CCc1ccccc1)C(=O)OC(C)(C)C]<br>n = 0<br>R¹ = 2-aminobutyric acid side chain<br>R² = H<br>R³ = CH(CH₃)₃ | (I)-o | (2-([1,1'-biphenyl]-4-ylmethyl)-3-((1-(tert-butoxy)-1-oxobutan-2-yl)amino)-3-oxopropyl)(phenethyl)phosphinic acid |

TABLE 1-continued

| Structure | Name |
|---|---|
| n = 0<br>R¹ = α-amino-2-naphthalenepropionic acid acid side chain<br>R² = H<br>R³ = benzyl | (I)-p (2-([1,1'-biphenyl]-4-ylmethyl)-3-((1-(benzyloxy)-3-(naphthalen-2-yl)-1-oxopropan-2-yl)amino)-3-oxopropyl)(phenethyl)phosphinic acid |
| n = 0<br>R¹ = cyclohexylglycine side chain<br>R² = H<br>R³ = Methyl | (I)-q (2-([1,1'-biphenyl]-4-ylmethyl)-3-((1-cyclohexyl-2-methoxy-2-oxoethyl)amino)-3-oxopropyl)(phenethyl)phosphinic acid |
| n = 0<br>R¹ = alanine side chain<br>R² = Methyl<br>R³ = Methyl | (I)-r (2-([1,1'-biphenyl]-4-ylmethyl)-3-((1-methoxy-2-methyl-1-oxopropan-2-yl)amino)-3-oxopropyl)(phenethyl)phosphinic acid |

Particularly advantageous stereoisomers according to the present invention are the ones listed in table 2:

TABLE 2

| Name | |
|---|---|
| ((S)-2-([1,1'-biphenyl]-4-ylmethyl)-3-(((S)-3-(benzo[b]thiophen-3-yl)-1-methoxy-1-oxopropan-2-yl)amino)-3-oxopropyl)(phenethyl)phosphinic acid | (I)-A |
| ((2S)-3-([1,1'-biphenyl]-4-yl)-2-((hydroxy(phenethyl)phosphoryl)methyl)propanoyl)-L-alloisoleucine | (I)-B |
| ((2S)-3-([1,1'-biphenyl]-4-yl)-2-((hydroxy(phenethyl)phosphoryl)methyl)propanoyl)-L-tryptophan salt with 2,2,2-trifluoroacetic acid (1:1) | (I)-C |

TABLE 2-continued

| Name | |
|---|---|
| ((R)-2-([1,1'-biphenyl]-4-ylmethyl)-3-(((S)-4-((tert-butoxycarbonyl)amino)-1-methoxy-1-oxobutan-2-yl)amino)-3-oxopropyl)(phenethyl)phosphinic acid | (I)-D |
| ((S)-2-([1,1'-biphenyl]-4-ylmethyl)-3-(((S)-1-(tert-butoxy)-4-methyl-1-oxopentan-2-yl)amino)-3-oxopropyl)(phenethyl)phosphinic acid | (I)-F |
| ((R)-2-([1,1'-biphenyl]-4-ylmethyl)-3-(((S)-1-(benzyloxy)-3-(naphthalen-2-yl)-1-oxopropan-2-yl)amino)-3-oxopropyl)(phenethyl)phosphinic acid | (I)-G |
| ((S)-2-([1,1'-biphenyl]-4-ylmethyl)-3-(((S)-1-methoxy-1-oxohexan-2-yl)amino)-3-oxopropyl)(phenethyl)phosphinic acid | (I)-H |
| ((2R)-3-([1,1'-biphenyl]-4-yl)-2-((hydroxy(phenethyl)phosphoryl)methyl)propanoyl)-L-asparagine | (I)-I |
| ((2S)-3-([1,1'-biphenyl]-4-yl)-2-((hydroxy(phenethyl)phosphoryl)methyl)propanoyl)-L-alanine | (I)-J |
| ((2R)-3-([1,1'-biphenyl]-4-yl)-2-((hydroxy(phenethyl)phosphoryl)methyl)propanoyl)-L-tryptophan compound with 2,2,2-trifluoroacetic acid (1:1) | (I)-K |
| 4-(3-([1,1'-biphenyl]-4-yl)-2-((hydroxy(phenethyl)phosphoryl)methyl)propanamido)butyric acid | (I)-L |
| (2S)-2-((2R)-3-([1,1'-biphenyl]-4-yl)-2-((hydroxy(phenethyl)phosphoryl)methyl)propanamido)-3-(benzo[b]thiophen-3-yl)propanoic acid | (I)-M |
| (2S)-2-((2R)-3-([1,1'-biphenyl]-4-yl)-2-((hydroxy(phenethyl)phosphoryl)methyl)propanamido)hexanoic acid | (I)-N |
| ((2S)-3-([1,1'-biphenyl]-4-yl)-2-((hydroxy(phenethyl)phosphoryl)methyl)propanoyl)-L-asparagine | (I)-O |
| ((S)-2-([1,1'-biphenyl]-4-ylmethyl)-3-(((S)-1-(tert-butoxy)-1-oxobutan-2-yl)amino)-3-oxopropyl)(phenethyl)phosphinic acid | (I)-P |
| ((S)-2-([1,1'-biphenyl]-4-ylmethyl)-3-(((S)-1-(benzyloxy)-3-(naphthalen-2-yl)-1-oxopropan-2-yl)amino)-3-oxopropyl)(phenethyl)phosphinic acid | (I)-Q |
| (2-([1,1'-biphenyl]-4-ylmethyl)-3-(((S)-1-(tert-butoxy)-3-(1-(tert-butoxycarbonyl)-1H-indol-3-yl)-1-oxopropan-2-yl)amino)-3-oxopropyl)(phenethyl)phosphinic acid | (I)-R |
| ((S)-2-([1,1'-biphenyl]-4-ylmethyl)-3-(((S)-1-cyclohexyl-2-methoxy-2-oxoethyl)amino)-3-oxopropyl)(phenethyl)phosphinic acid | (I)-S |
| ((R)-2-([1,1'-biphenyl]-4-ylmethyl)-3-(((2S,3R)-1-(tert-butoxy)-3-methyl-1-oxopentan-2-yl)amino)-3-oxopropyl)(phenethyl)phosphinic acid | (I)-T |
| ((S)-2-([1,1'-biphenyl]-4-ylmethyl)-3-(((2S,3R)-1-(tert-butoxy)-3-methyl-1-oxopentan-2-yl)amino)-3-oxopropyl)(phenethyl)phosphinic acid | (I)-U |
| (2-([1,1'-biphenyl]-4-ylmethyl)-3-((1-methoxy-2-methyl-1-oxopropan-2-yl)amino)-3-oxopropyl)(phenethyl)phosphinic acid | (I)-V |

The compounds of formula (I) according to the present invention can be prepared as outlined below and illustrated in the examples:

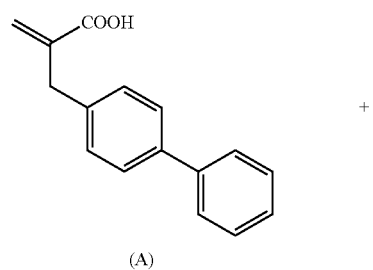

(A)

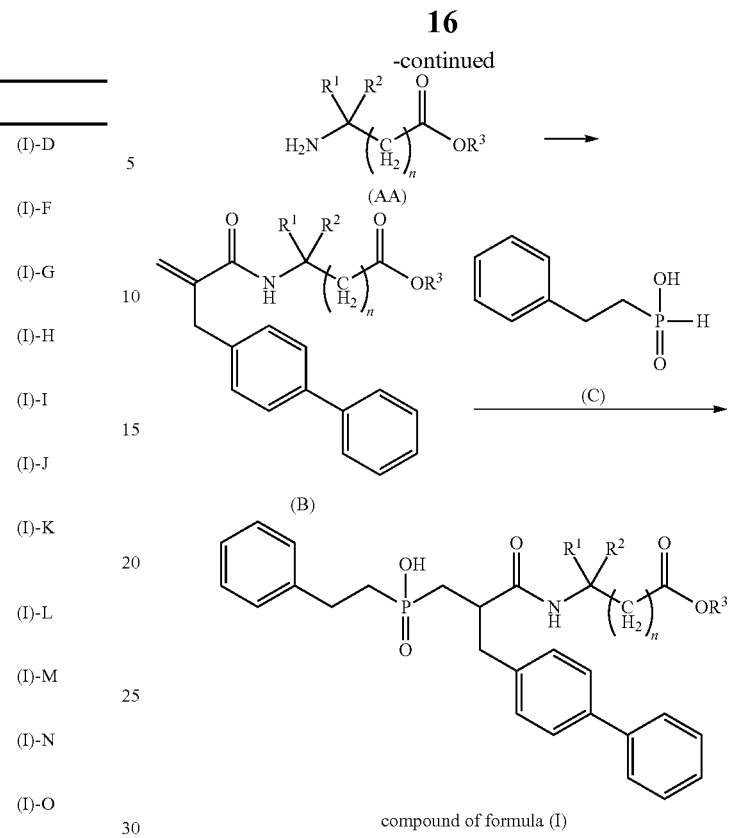

compound of formula (I)

2-Biphenyl-4-yl-acrylic acid (A) is coupled with an appropriate ester of the respective amino acid (AA; $R^3 \neq H$) using common coupling techniques as e.g. outlined in Peptide chemistry: A practical textbook by M Bodansky (Springer-Verlag, Heidelberg. 1988). The resulting intermediate (B) is subsequently condensed with (2-phenylethyl)phosphinic acid (C) as outlined in Chen et al (J. Med. Chem 2000, 43, pp 1398-1408) resulting in compounds of formula (I) wherein $R^3 \neq H$, which may then be subjected to ester hydrolyses e.g. using trifluoro acetic acid in dichloromethane to yield the corresponding compounds of formula (I) wherein $R^3 = H$.

The thus obtained diastereomeric mixtures may be used as such or may further be separated by chromatographic methods known in the art such as e.g. preparative HPLC (High Performance Liquid Chromatography).

In a second aspect, the present invention relates to cosmetic compositions comprising a compound of formula (I) with all the definitions and preferences as given above and a cosmetically acceptable carrier.

In yet another embodiment the present invention relates to the use of a compound of a formula (I) with all the definitions and preferences as given herein as MMP-12 inhibitor, in particular for the protection of elastin and/or collagen (by a reduction of the degradation of elastin/collagen by MMP-12), particular in aged and/or photo damaged skin.

Furthermore, the invention relates to the use of a compound of a formula (I) with all the definitions and preferences as given herein for the protection of elastin against UV-A light induced degradation.

It is particular preferred that the uses according to the present invention are a cosmetic uses, i.e. for the cosmetic treatment of the human skin (to beautify the skin).

As an increased protection of elastin and/or collagen leads to a reduction of the signs of skin aging such as to a reduction of wrinkles, fine lines, sagging, and laxity, the invention also relates to a method for preventing and/or treating aged or senescent skin such as preferably to smoothen wrinkles and fine lines, to decrease their volume and depth, and/or to treat skin sagging and to improve skin firmness said method comprising the step of applying a cosmetic composition according to the present invention with all the definitions and preferences given herein to the affected area and optionally appreciating the effect.

In another embodiment the invention relates to a method to protect the extracellular matrix proteins such as in particular elastin and/or collagen, said method comprising the step of applying a cosmetic composition according to the present invention with all the definitions and preferences given herein to an area in need thereof.

The term 'cosmetic composition' refers to compositions, which are used to treat, care for or improve the appearance of the skin and/or the scalp. Particular advantageous cosmetic compositions are skin care compositions.

The cosmetic compositions according to the invention are preferably intended for topical application, which is to be understood as the external application to keratinous substances, such as in particular the skin.

The term 'cosmetically acceptable carrier' as used herein refers to a physiologically acceptable medium which is compatible with keratinous substances. Suitable carriers are well known in the art and are selected based on the end-use application. Preferably, the carriers of the present invention are suitable for application to skin (e.g., sunscreens, creams, milks, lotions, masks, serums, hydrodispersions, foundations, creams, creamgels, or gels etc.). Such carriers are well known to one of ordinary skill in the art, and can include one or more compatible liquid or solid filler diluent, excipient, additive or vehicle, which are suitable for application to skin. The exact amount of carrier will depend upon the level of the compound of formula (I) and any other optional ingredients that one of ordinary skill in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The cosmetic compositions of the present invention can be formulated into a wide variety of product types, including creams, waxes, pastes, lotions, milks, mousses, gels, oils, tonics, and sprays. Preferably the compounds of formula (I) are formulated into lotions, creams, gels, and sprays. These product forms may be used for a number of applications, including, but not limited to, hand and body lotions, facial moisturizers, anti-ageing preparations, make-ups including foundations, and the like. Any additional components required to formulate such products vary with product type and can be routinely chosen by one skilled in the art.

If compositions of the present invention are formulated as an aerosol and applied to the skin as a spray-on product, a propellant is added to the composition.

The amount of the compound of formula (I) in the cosmetic composition can easily be adjusted by a person skilled in the art in order to achieve the desired beneficial effect.

Preferably, the amount of the compound of formula (I) in the cosmetic compositions according to the present invention is at least 1 ppm based on the total weight of the cosmetic composition. In all embodiments of the present invention the amount of the compound of formula (I) is preferably selected in the range of about 0.00001 to 0.5 wt.-%, more preferably in the range of 0.0001 to 0.25 wt.-%, most preferably in the range of 0.0001 to 0.1 wt.-% based on the total weight of the cosmetic composition.

The cosmetic compositions according to the present invention can be prepared by conventional methods in the art such as e.g. by admixing a compound of formula (I) with all the definitions and preferences given herein with the cosmetically acceptable carrier.

The cosmetic compositions of the invention (including the carrier) may comprise further conventional cosmetic adjuvants and additives, such as preservatives/antioxidants, fatty substances/oils, water, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the cosmetic compositions according to the invention may also comprise further cosmetically active ingredients conventionally used in cosmetic compositions. Exemplary active ingredients encompass skin lightening agents; UV-filters, agents for the treatment of hyperpigmentation; agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the cosmetic excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The cosmetic compositions according to the present invention may be in the form of a suspension or dispersion in solvents or fatty substances, or alternatively in the form of an emulsion or micro emulsion, in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

If the cosmetic composition is an emulsion, such as in particular an O/W, W/O, Si/W, W/Si, O/W/O, W/O/W multiple or a pickering emulsion, then the amount of the oily phase present in such cosmetic emulsions is preferably at least 10 wt.-%, such as in the range of 10 to 60 wt.-%, preferably in the range of 15 to 50 wt.-%, most preferably in the range of 15 to 40 wt.-%, based on the total weight of the cosmetic composition.

In one embodiment, the cosmetic compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art.

If the cosmetic composition according to the invention is an O/W emulsion, then it contains advantageously at least one O/W- or Si/W-emulsifier selected from the list of, glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-%, such as more in particular in the range of 0.5 to 5 wt.-%, such as most in particular in the range of 1 to 4 wt.-%, based on the total weight of the cosmetic composition.

Particular suitable O/W emulsifiers to be used in the cosmetic compositions according to the invention encompass phosphate ester emulsifiers such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate.

A particular suitable O/W emulsifier to be used in the cosmetic compositions according to the invention is potassium cetyl phosphate e.g. commercially available as Amphisol® K at DSM Nutritional Products Ltd Kaiseraugst.

Another particular suitable class of O/W emulsifiers are non-ionic self-emulsifying systems derived from olive oil e.g. known as (INCI Name) cetearyl olivate and sorbitan olivate (chemical composition: sorbitan ester and cetearyl ester of olive oil fatty acids) sold under the tradename OLIVEM 1000.

In one particular embodiment, the invention relates to cosmetic compositions with all the definitions and preferences given herein in the form of O/W emulsions comprising an oily phase dispersed in an aqueous phase in the presence of an O/W emulsifier wherein the O/W emulsifier is potassium cetyl phosphate. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%.

The cosmetic compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), tromethamine (Trizma Base) and aminomethylpPropanol (AMP-Ultra PC 2000), according to standard methods in the art.

The amount of the cosmetic composition to be applied to the skin is not critical and can easily be adjusted by a person skilled in the art. Preferably, the amount is selected in the range of 0.1 to 3 mg/cm$^2$ skin, such as preferably in the range of 0.1 to 2 mg/cm$^2$ skin and most preferably in the range of 0.5 to 2 mg/cm$^2$ skin.

Further suitable uses of the compounds according to the present invention encompass pharmaceutical applications. Thus, the compounds according to the present invention may be used to prepare a pharmaceutical composition together with a pharmaceutical acceptable carrier, diluent or excipient for the treatment, prevention and/or prophylaxis of any disorder and disease where it is desirable to inhibit MMP-12 in a patient in need thereof such as e.g. for the treatment, prevention and/or prophylaxis of cancer, rheumatoid arthritis, osteoarthritis.

The invention is further illustrated with reference to the following, non-limiting examples, in which all percentages are by weight based on total weight unless otherwise specified.

EXPERIMENTAL PART

1. General Information

| Abbreviations: | |
|---|---|
| AA | Amino acid |
| DMF: | N,N-dimethylformamide |
| EtOAc: | Ethyl acetate |
| DCM: | Dichloromethane |
| MeCN: | Acetonitrile |
| DIPEA: | N,N-diisopropylethylamine |
| BTU: | O-(Benzotriazol-1-yl)-N,N,N',N'-tetramethyluronium-tetrafluoroborate |
| BSA: | N,O-bis(trimethylsilyl)acetamide |
| TFA: | Trifluoroacetic acid |
| n.a.: | not analyzed |
| FCS | fetal calf serum |
| P/S | Penicillin/Streptomycin |
| TGFb1 | transforming growth factor, beta 1 |
| HBSS | Hank's Balanced Salt Solution |
| PBS | Phosphate-Buffered Saline |
| BSA | Bovine serum albumin |

MS/HPLC-spectra were measured on a Waters Alliance 2695 HPLC system, equipped with a Waters Symmetry C18, 3.5 µm, 4.6 mm×50 mm analytical column and with a Waters 2996 photodiode array detector (PDA) operating in the 200-400 nm wavelength range coupled to a Waters ZQ 4000 (Single Quadrupole Detector) mass spectrometer operating in positive electrospray ionization (ESI+) mode and detecting in the m/z range 100-1500. $H_2O$+0.07% TFA (A phase) and MeCN+0.07% TFA (B phase) were used as eluents, with a flow rate of 1.0 mL/min.

Preparative HPLC Purifications:

performed on a Waters Prep LC 2000 system equipped with a Grom Saphir 110, C18, 10 μm, 50 mm×300 mm preparative column and a Waters 2487 dual wavelength UV-Vis detector operating at 220 nm and 254 nm.

$H_2O$+0.07% TFA (A phase) and MeCN+0.07% TFA (B phase) were used as eluents, with a flow rate of 65 mL/min.

In the following the preparation of two compounds according to the invention is illustrated (I)-J and (I)-N. The others compounds outlined in Table 1, 2 and Table 3 have been prepared accordingly.

Example 1

Preparation of ((2S)-3-([1,1'-biphenyl]-4-yl)-2-((hydroxy(phenethyl)phosphoryl)methyl)-propanoyl)-L-alanine (I)-J and ((2R)-3-([1,1'-biphenyl]-4-yl)-2-((hydroxyl-(phenethyl)-phosphoryl)methyl) propanoyl)-L-alanine (I)-J'

350 mg (1.47 mmol) of 2-biphenyl-4-yl-acrylic acid was dissolved in 4 ml of DMF and chilled to 5° C. Subsequently 495 mg TBTU and 512 μl DIPEA were added, followed by a solution of 320 mg of H-Ala-OtBu.HCl (1.76 mmol) in 3 ml of DMF along with 299 μl of DIPEA. After stirring for 30 min at 5° C. and overnight at RT, the crude product was isolated by evaporation of solvent. The residue was dissolved in 30 ml of EtOAc and washed consecutively with 10% citric acid, 10% $NaHCO_3$ and saturated NaCl-solution. After drying over $Na_2SO_4$ and evaporation of solvent, 500 mg of an oil was obtained. HPLC (220 nm)—95%, $[M+H]^+$, found 366 (theo. 366). The obtained intermediate (475 mg, 1.3 mmol) was dissolved in 5 ml of BSA along with 265 mg (1.56 mmol) of (2-phenethyl)-phosphinic acid under a stream of argon, followed by heating to ca. 70° C. for 62 h (94% conversion). The reaction mixture was diluted with 100 ml of EtOAc and BSA quenched by addition of 10 ml of water. After washing thoroughly with fresh water and saturated NaCl-solution, drying over $Na_2SO_4$, filtering and evaporation of solvent, 630 mg of a yellowish oil was obtained. The crude product was chromatographed using preparative HPLC to separate the two formed diastereomers yielding after lyophilisation:

295 mg of (2-([1,1'-biphenyl]-4-ylmethyl)-3-(−1-(tert-butoxy)-1-oxopropan-2-yl)amino)-3-oxopropyl)(phenethyl) phosphinic acid consisting mainly of the (S/S)-isomer (80%) and 146 mg consisting of mainly the (R/S)-isomer (82%)).

ESI-MS $[M+H]^+$: found 536.4 for both peaks (theo: 536.3).

Each fraction was hydrolyzed to the corresponding acid by dissolving the respective compound in 2 ml of DCM and adding 2 ml of 95% TFA. Upon completion of hydrolysis of the ester and evaporation of the solvent, the crude products were chromatographed with preparative HPLC yielding 171 mg of (I)-J as colorless powder, purity: 98% (HPLC), ESI-MS $[M+H]^+$: 480.3 (theo: 480.2) and 62 mg of (I)-J' as off-white powder, purity: 97% (HPLC), ESI-MS $[M+H]^+$: found 480.3 (theo: 480.2).

Example 2

((S)-2-([1,1'-biphenyl]-4-ylmethyl)-3-(((S)-1-methoxy-1-oxohexan-2-yl)amino)-3-oxopropyl) (phenethyl)phosphinic acid (I)-H and (2S)-2-((2R)-3-([1,1'-biphenyl]-4-yl)-2-((hydroxy(phenethyl) phosphoryl)methyl)propanamido)hexanoic acid (I)-N 350 mg (1.47 mmol) of 2-biphenyl-4-yl-acrylic acid was dissolved in 4 ml of DMF and chilled to 5° C. Subsequently 495 mg TBTU and 512 μl DIPEA were added, followed by a solution of 320 mg of H—NIe-OMe.HCl (1.76 mmol) in 3 ml of DMF along with 299 μl of DIPEA. After stirring for 30 min at 5° C. and overnight at RT, the crude product was isolated by evaporation of solvent. The residue was dissolved in 30 ml of EtOAc and washed consecutively with 10% citric acid, 10% $NaHCO_3$ and saturated NaCl-solution. After drying over $Na_2SO_4$, filtration and evaporation of solvent, 523 mg of an oil was obtained. HPLC (220 nm)— 83%, LC-MS: $[M+H]^+$, found 366 (theo. 366). The intermediate (523 mg, 1.33 mmol) was dissolved in 5 ml of BSA along with 285 mg (1.68 mmol) of (2-phenethyl)-phosphinic acid under a stream of argon, followed by heating to ca. 70° C. After 15 h, HPLC monitoring indicated approx. 70% conversion. Fresh BSA along with 200 mg of (2-phenethyl)-phosphinic acid was added and stirring continued under argon for a total of 4 days. The reaction mixture was diluted with 100 ml of EtOAc and BSA quenched by addition of 10 ml water. After washing thoroughly with fresh water and saturated NaCl-solution, drying over $Na_2SO_4$, filtration and evaporation of solvent, 710 mg of a yellowish oil was obtained. The crude product was chromatographed using preparative HPLC to separate the two formed diastereomers yielding after lyophilization 36 mg of ((S)-2-([1,1'-biphenyl]-4-ylmethyl)-3-(((S)-1-methoxy-1-oxohexan-2-yl)amino)-3-oxopropyl)(phenethyl) phosphinic acid (I)-H as off-white powder and 69 mg of ((R)-2-([1,1'-biphenyl]-4-ylmethyl)-3-(((S)-1-methoxy-1-oxohexan-2-yl)amino)-3-oxopropyl)(phenethyl) phosphinic acid (I)-H' as off-white powder and 257 mg of a mixture of (I)-H (51%) and (I)-H' (47%)

ESI-MS $[M+H]^+$: found 536.4 for both peaks (theo: 536.3).

Each fraction was mildly saponified to the corresponding acid by dissolving in THF and adding 1.1 eq of LiOH. Upon completion of hydrolysis of the ester, each reaction mixture was acidified and extracted with EtOAc and the crude product chromatographed with preparative HPLC yielding 88 mg (2S)-2-((2S)-3-([1,1'-biphenyl]-4-yl)-2-((hydroxy (phenethyl)phosphoryl)methyl)-propanamido)hexanoic acid (I)-N' as off-white powder. Purity: 99% (HPLC); ESI-MS $[M+H]^+$: found 522.2 (theo: 522.2) and 80 mg (2S)-2-((2R)-3-([1,1'-biphenyl]-4-yl)-2-((hydroxy (phenethyl)phosphoryl)methyl)-propanamido)hexanoic acid (I)-N as off-white powder. Purity 90% (HPLC); ESI-MS $[M+H]^+$: found 522.2 (theo: 522.2)

Example 3: Inhibition of MMP-12

The MMP-12 inhibitor activity was quantified by fluorometric analysis using the MMP-12 Fluorometric Drug Discovery Kit (Enzo Life Sciences Inc., Farmingdale, N.Y., USA) according to the manufacturers' instructions.

TABLE 3-1
| | | Results of the assay | | |
|---|---|---|---|---|
| | | | % Inhibition after 20 min | | |
| # | Compound | 10 μM | 1 μM | 0.5 μM |
| 1 | 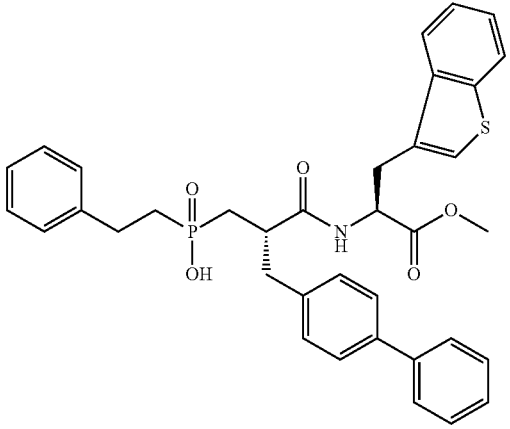 [SMILES: COC(=O)[C@H](Cc1csc2ccccc12)NC(=O)[C@H](Cc1ccc(-c2ccccc2)cc1)CP(=O)(O)CCc1ccccc1]<br>(I)-A | 92 | 82 | 75 |
| 2 | 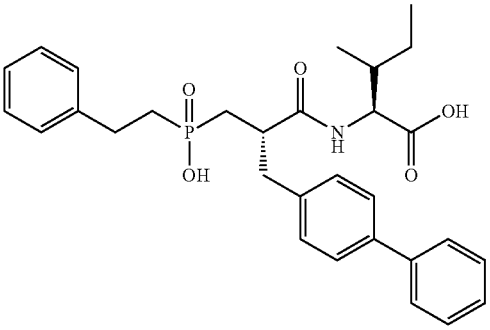 [SMILES: CCC(C)[C@H](NC(=O)[C@H](Cc1ccc(-c2ccccc2)cc1)CP(=O)(O)CCc1ccccc1)C(=O)O]<br>(I)-B | 92 | 94 | 94 |
| 3 | 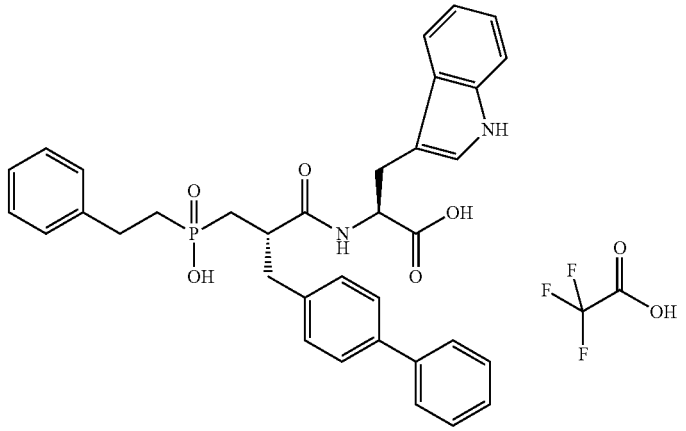 [SMILES: O=C(N[C@@H](Cc1c[nH]c2ccccc12)C(=O)O)[C@H](Cc1ccc(-c2ccccc2)cc1)CP(=O)(O)CCc1ccccc1 ; O=C(O)C(F)(F)F]<br>(I)-C | 92 | 94 | 93 |

TABLE 3-1-continued
| | | Results of the assay | | |
|---|---|---|---|---|
| | | | % Inhibition after 20 min | | |
| # | Compound | 10 μM | 1 μM | 0.5 μM |
| 4 | 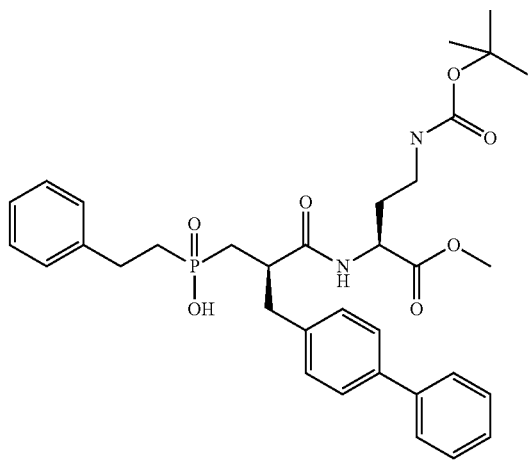 [SMILES: COC(=O)[C@H](CCNC(=O)OC(C)(C)C)NC(=O)[C@@H](Cc1ccc(-c2ccccc2)cc1)CP(=O)(O)CCc1ccccc1] (I)-D | 91 | 90 | 85 |
| 5 | 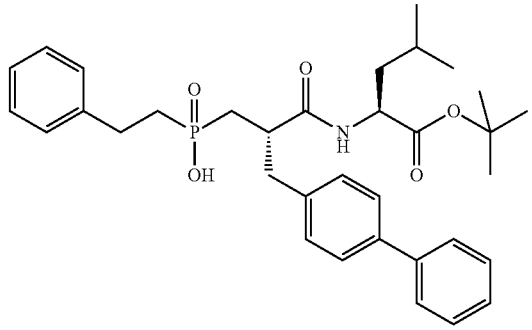 [SMILES: CC(C)C[C@H](NC(=O)[C@H](Cc1ccc(-c2ccccc2)cc1)CP(=O)(O)CCc1ccccc1)C(=O)OC(C)(C)C] (I)-F | 91 | 82 | 73 |
| 6 | 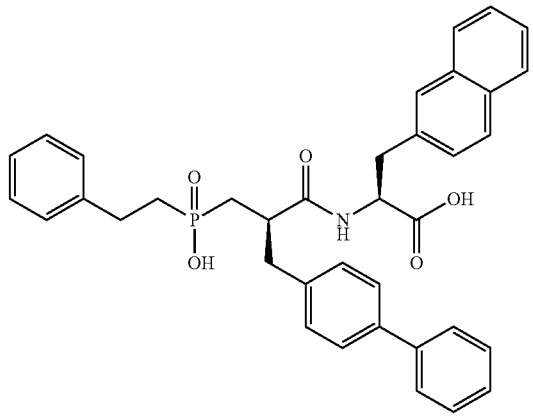 [SMILES: O=C(N[C@@H](Cc1ccc2ccccc2c1)C(=O)O)[C@@H](Cc1ccc(-c2ccccc2)cc1)CP(=O)(O)CCc1ccccc1] (I)-G | 91 | 85 | 78 |

TABLE 3-1-continued

Results of the assay

| # | Compound | % Inhibition after 20 min | | |
|---|---|---|---|---|
| | | 10 μM | 1 μM | 0.5 μM |
| 7 | (I)-H | 91 | 89 | 83 |
| 8 | (I)-I | 90 | 89 | 84 |
| 9 | (I)-J | 90 | 94 | 93 |
| 10 | (I)-K | 90 | 79 | 69 |

TABLE 3-1-continued
Results of the assay
| # | Compound | % Inhibition after 20 min | | |
|---|---|---|---|---|
| | | 10 μM | 1 μM | 0.5 μM |
| 11 | 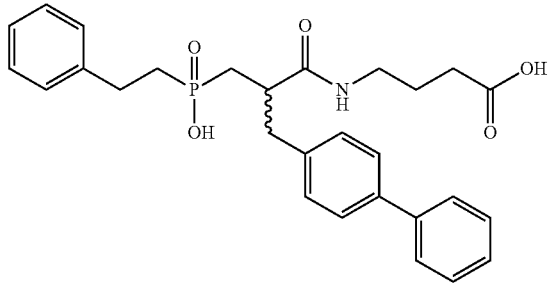 [SMILES: O=C(O)CCCNC(=O)C(Cc1ccc(-c2ccccc2)cc1)CP(=O)(O)CCc1ccccc1] (I)-L | 90 | 82 | 75 |
| 12 | 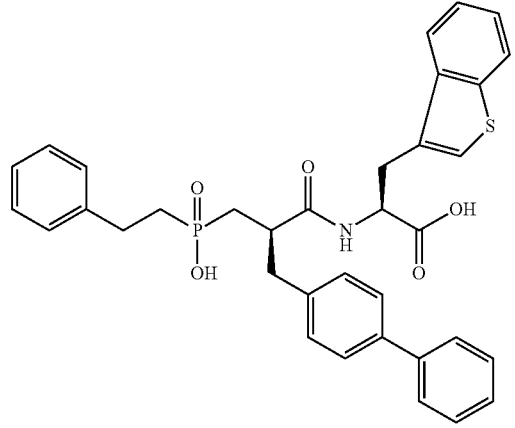 [SMILES: O=C(N[C@@H](Cc1csc2ccccc12)C(=O)O)[C@@H](Cc1ccc(-c2ccccc2)cc1)CP(=O)(O)CCc1ccccc1] (I)-M | 89 | 64 | 52 |
| 13 | 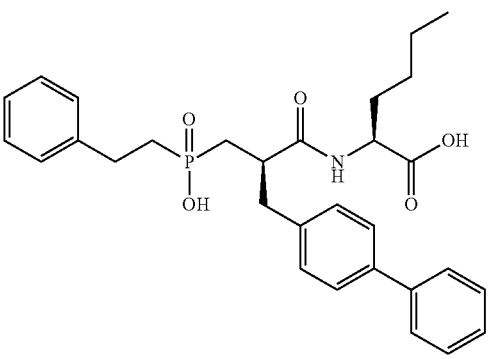 [SMILES: CCCC[C@H](NC(=O)[C@@H](Cc1ccc(-c2ccccc2)cc1)CP(=O)(O)CCc1ccccc1)C(=O)O] (I)-N | 89 | n.a. | n.a. |
| 14 | 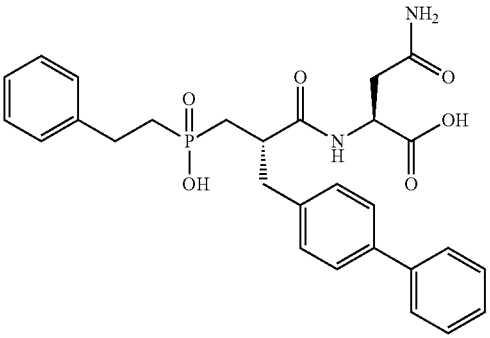 [SMILES: NC(=O)C[C@H](NC(=O)[C@H](Cc1ccc(-c2ccccc2)cc1)CP(=O)(O)CCc1ccccc1)C(=O)O] (I)-O | 88 | n.a. | n.a. |

TABLE 3-1-continued
| | | Results of the assay | | |
| | | % Inhibition after 20 min | | |
| # | Compound | 10 μM | 1 μM | 0.5 μM |
| 15 | (I)-P | 88 | n.a. | n.a. |
| 16 | (I)-Q | 83 | n.a. | n.a. |
| 17 | (I)-R | 82 | n.a. | n.a. |
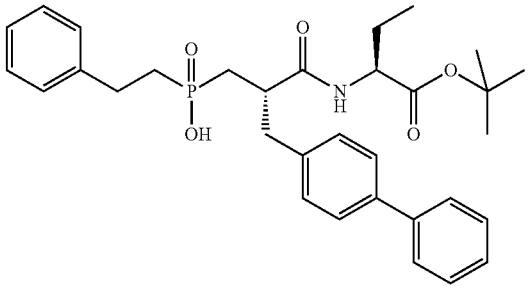 [SMILES: CC[C@H](NC(=O)[C@H](Cc1ccc(-c2ccccc2)cc1)CP(=O)(O)CCc1ccccc1)C(=O)OC(C)(C)C]
(I)-P
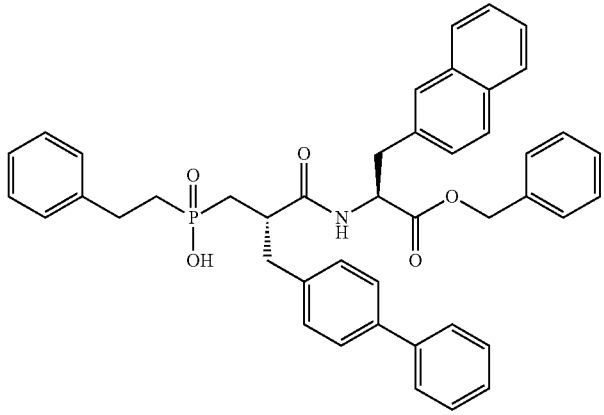 [SMILES: O=C(N[C@@H](Cc1ccc2ccccc2c1)C(=O)OCc1ccccc1)[C@H](Cc1ccc(-c2ccccc2)cc1)CP(=O)(O)CCc1ccccc1]
(I)-Q
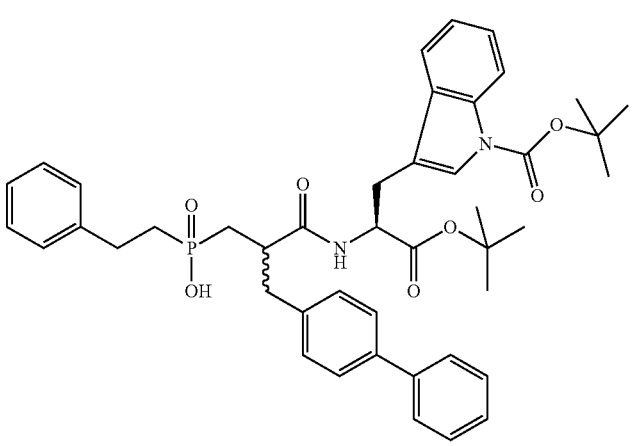 [SMILES: CC(C)(C)OC(=O)[C@H](Cc1cn(C(=O)OC(C)(C)C)c2ccccc12)NC(=O)C(Cc1ccc(-c2ccccc2)cc1)CP(=O)(O)CCc1ccccc1]
(I)-R TABLE 3-1-continued
Results of the assay
| # | Compound | % Inhibition after 20 min | | |
|---|---|---|---|---|
|   |   | 10 μM | 1 μM | 0.5 μM |
| 18 | 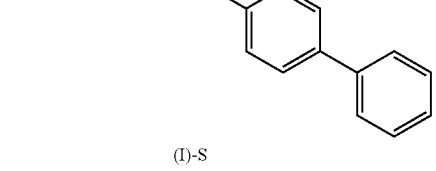 (I)-S | 82 | n.a. | n.a. |
| 19 | 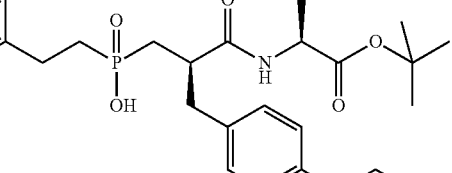 (I)-T | 75 | n.a. | n.a. |
| 20 | 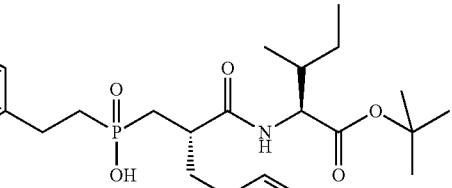 (I)-U | 72 | n.a. | n.a. |
| 21 | 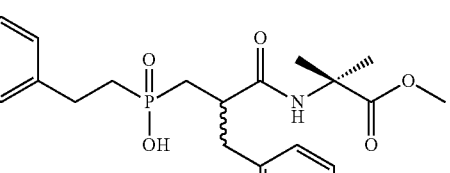 (I)-V | 61 | n.a. | n.a. |

Example 4-1: Inhibition of the Degradation of the Elastin Fibers Produced by Human Dermal Fibroblasts Human dermal fibroblasts were pre-cultured in DMEM, 10% FCS, 1% P/S for 48 hrs before starving them in DMEM, 0.2% FCS, 1% P/S for 24 hrs. To induce elastin fiber production TGFb1 (10 ng/ml) was added and incubated for 5 days. After incubation with TGFb1, medium was carefully discarded and cells were washed with assay buffer (HBSS, 25 µM HEPES). In the meantime MMP-12 (200 U/ml) and compounds were mixed in assay buffer and allowed to interact for 30 min. This mixture was then added to the cells and incubated for 2 hrs at 37° C.

Cells were then fixed with ice-cold methanol for 5 min and rehydrated by PBS. Unspecific sites were blocked with 1% BSA in PBS for 1 h at room temperature. Elastin fibers were detected using a primary antibody against elastin and the first antibody was detected with AlexaFluor 488 conjugated secondary antibody. Finally, nuclei were counter-stained with DAPI. Stained cells were analyzed with the Thermo Scientific ArrayScan XTI Live High Content Platform. 49 pictures per well were acquired with a 20× objective and as readout we used the area covered by the elastin fibers. % of inhibition of elastin fiber degradation was calculated the following way:

% protection of elastin fiber network degradation=100−[(max area−min area)/(max area inhibitor area)*100] in which max area=area covered by elastin fibers of untreated control cells
min area=area covered by elastin fibers of MMP12 treated cells
inhibitor area=area covered by elastin fibers of MMP12 and inhibitor treated cells.

The results are outlined below outlined in table 4-1.

TABLE 4-1

| | % protection of elastin fiber network degradation | | |
|---|---|---|---|
| Compound | 20 µM | 1 µM | 0.05 µM |
| (I)-C<sup>Δ</sup> | 92.03 | 84.78 | 44.07 |
| (I)-c* | 87.95 | 71.96 | 24.86 |
| (I)-J<sup>Δ</sup> | 91.72 | 68.42 | 26.46 |
| (I)-m* | 80.76 | 64.88 | 8.95 |
| (I)-B<sup>Δ</sup> | 90.12 | 81.75 | 17.38 |
| (I)-e* | 83.73 | 68.17 | 12.44 |
| (I)-k* | 98.72 | 84.79 | 25.93 |
| (I)-O<sup>Δ</sup> | 89.07 | 45.61 | 13.75 |
| (I)-l* | 105.48 | 54.65 | 18.25 |
| (I)-n* | 76.78 | 30.36 | 41.01 |

<sup>Δ</sup>Pure stereoisomer
*Mixture of stereoisomers

Example 4-2: Total Dermal Elastin after UV-Irradiation

Human skin from abdominal plastic surgery classified as "Intermediate" (ITA° angle=53°) has been used. The skin samples were cut in pieces of approx. 8×3 mm (ø×thickness) and cultured up to day 6 in an air-liquid interface in a perforated ring of stainless steel in contact with a culture medium (modified Williams'E medium), the culture medium was renewed every three days. Eight skin specimens were used for each treatment. Each test sample (4 µl) was topically applied twice a day, immediately after UV irradiation and renewed 4 hours later top of each piece after gentle cleaning of the surface with a cotton pad followed by covering with a 6 ømm delivery membrane, which procedure was repeated daily. The samples were irradiated daily with 800% of the Biological Effective Dose of daylight (BED; Del Bino et al, Pigment Cell research, 19, 2006) equal to a dose of 45 J/cm$^2$ UVA using an adopted BIO-SUN system (Vilber Lourmat). At day 6 twelve skin sections were immunostained with mouse monoclonal anti-Elastin antibody (Sigma cat#E4013). The papillary dermis is selected for the analysis. The evaluation has been performed by estimating both color intensity and distribution with IMAGE J (NIH) analysis software Two slides of each skin sample have been processed by image acquisition and related analysis (i.e. 12 images for each treatment). The score of the dermal Elastin of the non-UV treated sample was set to 100%.

TABLE 4-2

| | Dermal Elastin at day 6 | | |
|---|---|---|---|
| Treatment | Concentration [µm] | Dermal elastin [%] | Increase vs. untreated-UV |
| NO UV | — | 100 | |
| Untreated - UV | — | 81 | |
| (IV-c) - UV | 100 | 123 | +52% |
| (II-m) - UV | 100 | 106 | +30% |
| (IV-k) - UV | 100 | 125 | +54% |

((Dermal elastin sample − Dermal Elastin − UV)/Dermal Elastin UV * 100%)

As can be retrieved from the results outlined in table 4-2, the compounds according to the present invention counteracted UV damage while restoring or even enhancing dermal elastin in the papillary dermis.

Example 5: Cosmetic Composition

Table 5-1 outlines exemplary O/W emulsions, wherein one compound (eventually as mixture of stereoisomers) selected from the group of I (a-r) [Table 1] and (I)-(A-V) [Table 2], is incorporated in the indicated amount.

TABLE 5-1

| | Exemplary O/W emulsion | | | | | | | |
|---|---|---|---|---|---|---|---|---|
| O/W Emulsions | 1 | 2 | 3 | 4 | 5 | 6 | 7 | 8 |
| Glyceryl Stearate | 2.5 | 2 | 1.2 | 1 | | | 1 | 1 |
| PEG-40 Stearate | 1 | | | | | | | |
| PEG-100 Stearate | | 2.5 | | | | | | 1 |
| Ceteareth-20 | | | | | 1 | | | |
| Glyceryl Stearate Citrate | | | | | | 0.5 | | |
| Potassium Cetyl Phosphate | | | | | | | 3 | 1.5 |
| Stearic Acid | | | 2.5 | 3 | | | | |
| Cetearyl Alcohol | | 4 | | 2 | | | 2 | |

TABLE 5-1-continued

| O/W Emulsions | Exemplary O/W emulsion | | | | | | | |
|---|---|---|---|---|---|---|---|---|
| | 1 | 2 | 3 | 4 | 5 | 6 | 7 | 8 |
| Stearyl Alcohol | | 2 | 1 | | | | | |
| Cetyl Alcohol | | | 1 | 1 | | | | 0.5 |
| Acrylates/$C_{10\text{-}30}$ Alkyl Acrylate Crosspolymer | | | | 0.2 | 0.2 | 0.4 | 0.2 | |
| Carbomer | 0.1 | | 0.2 | | | | | |
| Xanthan Gum | | 0.3 | | | | | | 0.3 |
| $C_{12\text{-}15}$ Alkyl Benzoate | 5 | | 2 | 5 | 5 | 10 | 5 | |
| Petrolatum | 5 | | 3 | | | | | |
| Butylene Glycol Dicaprylate/Dicaprate | | 4 | 2 | | 9 | | | 9 |
| Hydrogenated Polydecene | | | 3 | | 2 | | | 2 |
| Caprylic/Capric Triglyceride | 1 | 3 | | 5 | | 5 | 5 | |
| Cyclomethicone | | 5 | 2 | | | 10 | | |
| Methylpropanediol | 2 | | | | 3 | | | 3 |
| Glycerine | 4 | 7 | 3 | 4 | 3 | | 5 | 3 |
| Glyceryl Glucoside | 3.5 | 3 | 1 | 1 | 2 | | | 2 |
| Alcohol denat. | 1 | 3 | 0.5 | 10 | 4 | 8 | | 4 |
| Butylene Glycol | | | 3 | | | | | |
| Ascorbylglucoside | | 0.5 | | 1.0 | | 1.5 | | 0.1 |
| Ubiquinone (Coenzyme 10) | 0.1 | | 0.05 | | | | 0.01 | |
| Hyaluronic acid | | | | 0.2 | | | 0.2 | |
| Bisabolol | 0.5 | | | | | | | |
| Isotridecylsalicylate | | | 1 | 3 | 5 | 2 | 3 | 5 |
| Compound selected from the group of I (a-r) and (I)-(A-V) | 0.001 | 0.25 | 0.0001 | 0.05 | 0.1 | 0.0003 | 0.03 | 0.002 |
| Dibutyl Adipate | 1.5 | 3 | | | | | | |
| Diisopropyl sebacate | | 1 | 1 | 2 | 3 | | | |
| Ethylhexyl Benzoate | | | | | | 0.75 | 1.5 | 1 |
| Titanium Dioxide (PARSOL TX) | | | 0.5 | 2 | | | | |
| Methylene Bis-Benztriazoyl Tetramethylbutylphenol | | | 0.5 | 4 | | 6 | | 2 |
| Ethylhexyl methoxycinnamate | | | | 2 | | | | |
| Phenylbenzimidazole Sulfonic Acid | | | | 2 | | 2 | 2 | |
| Butyl Methoxydibenzoylmethane | | 1 | | 2 | 2 | 3 | 3 | 3 |
| Methylbenzylidene Camphor | | | | 2 | 3 | | | |
| Octocrylene | | 5 | | 2 | | 2 | 10 | |
| Polysilicone-15 | | | | 2 | | 3 | | |
| Ethylhexyl Salicylate | | | | 5 | | | | |
| Homosalate | | | 4 | 2 | | | | |
| Bis-Ethylhexyloxyphenol Methoxyphenyltriazine | | 1.5 | | | | | | 2 |
| Silica | 1 | | 2.5 | | | 0.5 | | |
| Silica & Methicone | | 4 | | 1 | 2.5 | | | |
| Methyl Methacrylate Crosspolymer | | | | 1 | | | 2 | |
| Disodium EDTA | 0.1 | | | | | 0.5 | | |
| Fragrance, Preservatives | | | | q.s. | | | | |
| Sodium Hydroxide | | | | q.s. | | | | |
| Water | | | | Ad 100 | | | | |

The invention claimed is:

1. A compound of formula (I):

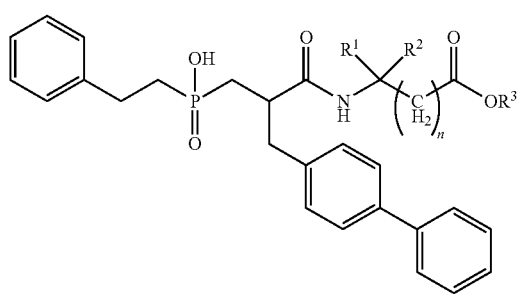

wherein
n is 0, 1 or 2,
R$^1$ is H, or an amino acid side chain which, if a functional group is present, may optionally be substituted by a $C_1$-$C_6$alkyl group, a $C_1$-$C_6$alkylcarbonyl group or a $C_1$-$C_6$alkoxycarbonyl group,
R$^2$ is H or methyl, and
R$^3$ is selected from the group consisting of H, a $C_1$-$C_6$ alkyl group and an aryl $C_1$-$C_6$alkanyl group or a cosmetically acceptable salt thereof.

2. The compound according to claim 1, wherein the amino acid side chain is a nonpolar or an uncharged polar side chain of an amino acid.

3. The compound according to claim 1, wherein the amino acid side chain is selected from the side chains of glutamine, phenylalanine, methionine, valine, glycine, 2,4-diaminobutyric acid, 2-aminobutyric acid, alanine, leucine, isoleucine, norleucine, tryptophan, thiotryptophan, cyclohexylglycine, α-amino-2-naphthalenepropionic acid, serine, threonine, tyrosine, proline, asparagine and cysteine.

4. The compound according to claim 1, wherein the amino acid side chain has a functional group which is substituted with a $C_1$-$C_6$alkoxycarbonyl group.

5. The compound according to claim 1, wherein
   n is 0, 1 or 2,
   $R^1$ is H or an amino acid side chain selected from the group consisting of thiotryptophan, isoleucine, tryptophan, 2,4-diaminobutyric acid, leucine, α-amino-2-naphthalenepropionic acid, norleucine, asparagine, alanine, 2-amino butyric acid, cyclohexylglycine, 2-amino-4-(tert-butoxycarbonylamino)butyric acid and 1-[(1,1-dimethylethoxy)carbonyl]-tryptophan
   $R^2$ is H or methyl, and
   $R^3$ is selected from the group consisting of H, a methyl group, a tert.-butyl group and a benzyl group,
   or a cosmetically acceptable salt thereof.

6. The compound according to claim 1, wherein
   n is 0 or 2,
   $R^1$ is H or an amino acid side chain selected from the group consisting of thiotryptophan, isoleucine, tryptophan, 2,4-diaminobutyric acid, leucine, α-amino-2-naphthalenepropionic acid, norleucine, asparagine, alanine, 2-amino butyric acid, cyclohexylglycine, 2-amino-4-(tert-butoxycarbonylamino)butyric acid and 1-[(1,1-dimethylethoxy)carbonyl]-tryptophan
   $R^2$ is H and
   $R^3$ is selected from the group consisting of H, a methyl group, a tert.-butyl group and a benzyl group,
   or a cosmetically acceptable salt thereof.

7. The compound according to claim 1, which is a compound selected from the group consisting of:

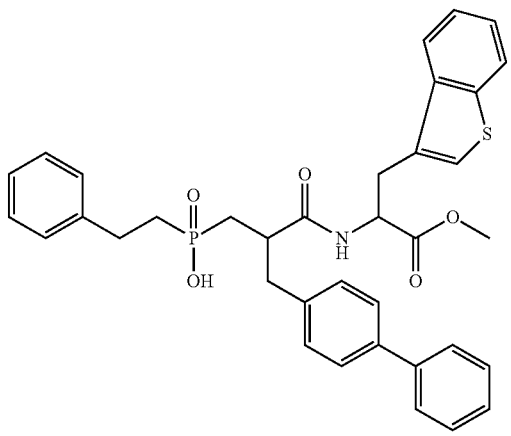 [SMILES: COC(=O)C(Cc1csc2ccccc12)NC(=O)C(Cc1ccc(-c2ccccc2)cc1)CP(=O)(O)CCc1ccccc1]

(I)-a

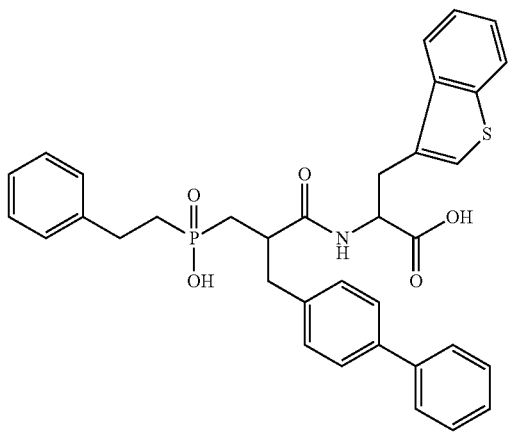 [SMILES: O=C(NC(Cc1csc2ccccc12)C(=O)O)C(Cc1ccc(-c2ccccc2)cc1)CP(=O)(O)CCc1ccccc1]

(I)-b

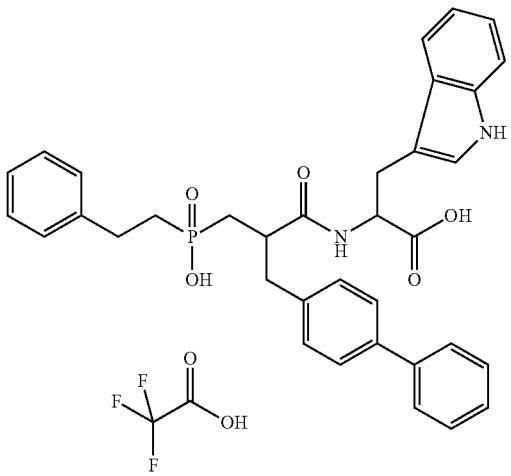 [SMILES: O=C(NC(Cc1c[nH]c2ccccc12)C(=O)O)C(Cc1ccc(-c2ccccc2)cc1)CP(=O)(O)CCc1ccccc1 ; O=C(O)C(F)(F)F]

(I)-c

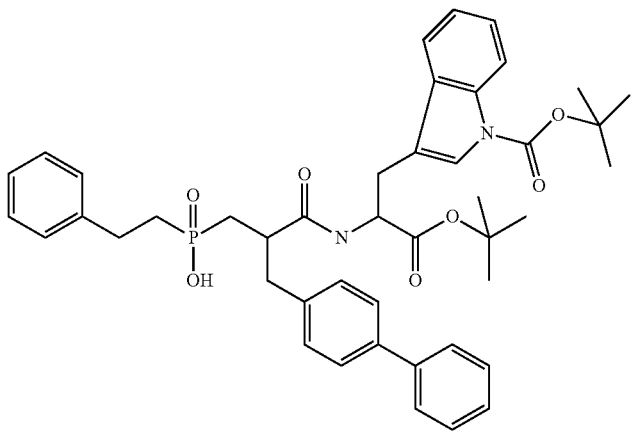 [SMILES: CC(C)(C)OC(=O)C(Cc1cn(C(=O)OC(C)(C)C)c2ccccc12)NC(=O)C(Cc1ccc(-c2ccccc2)cc1)CP(=O)(O)CCc1ccccc1]

(I)-d

-continued
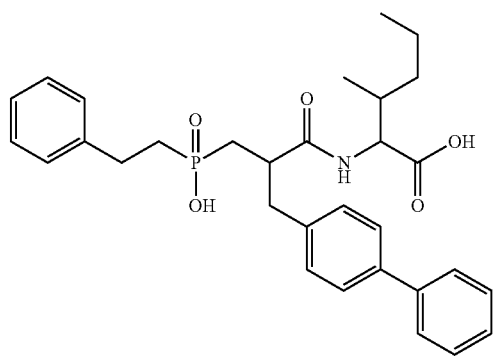 [SMILES: CCCC(C)C(NC(=O)C(Cc1ccc(-c2ccccc2)cc1)CP(=O)(O)CCc1ccccc1)C(=O)O]
(I)-e
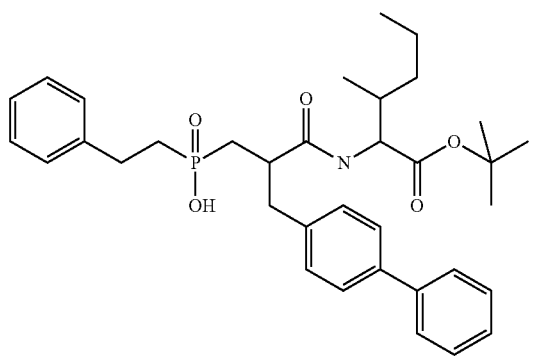 [SMILES: CCCC(C)C(NC(=O)C(Cc1ccc(-c2ccccc2)cc1)CP(=O)(O)CCc1ccccc1)C(=O)OC(C)(C)C]
(I)-f
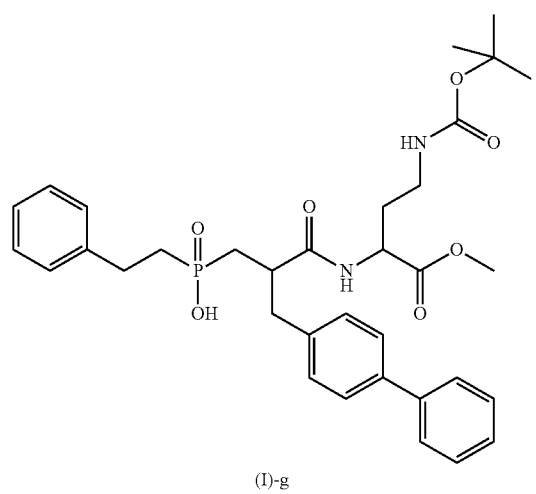
(I)-g
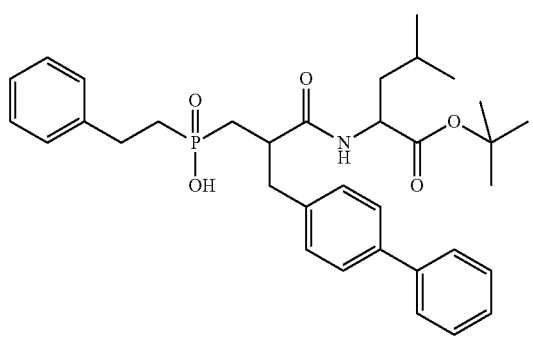 [SMILES: CC(C)CC(NC(=O)C(Cc1ccc(-c2ccccc2)cc1)CP(=O)(O)CCc1ccccc1)C(=O)OC(C)(C)C]
(I)-h
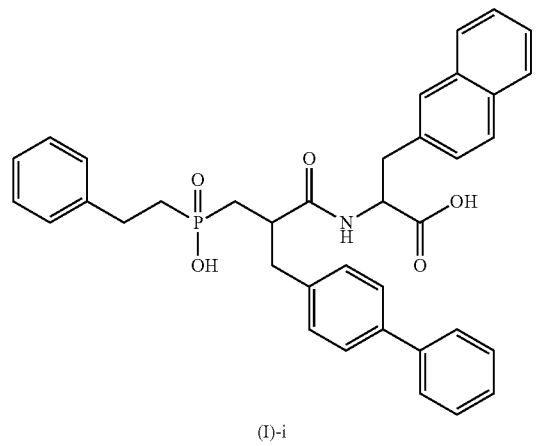
(I)-i
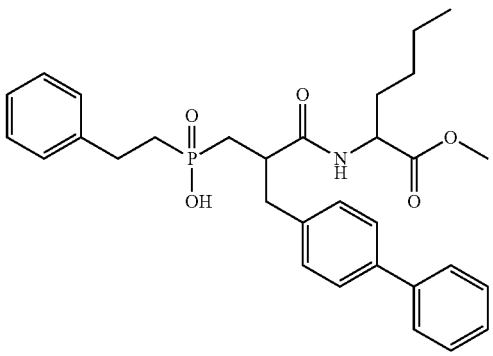 [SMILES: CCCCC(NC(=O)C(Cc1ccc(-c2ccccc2)cc1)CP(=O)(O)CCc1ccccc1)C(=O)OC]
(I)-j -continued
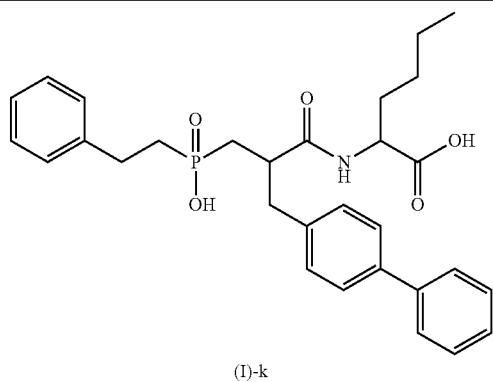
(I)-k
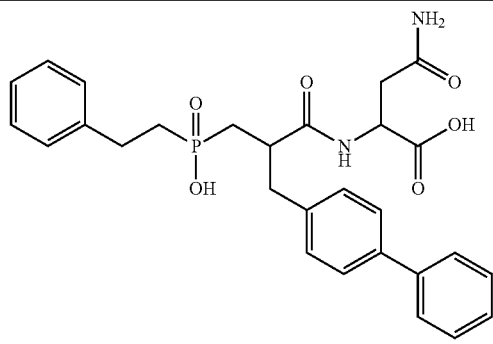
(I)-l
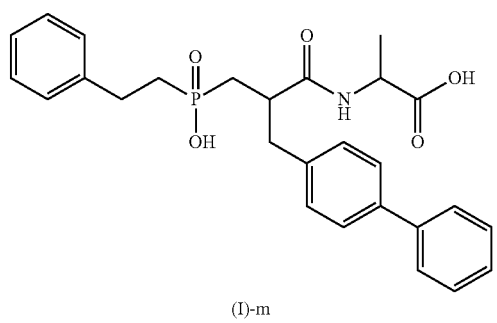
(I)-m
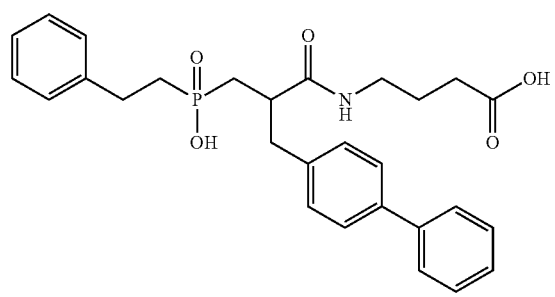 [SMILES: O=C(O)CCCNC(=O)C(Cc1ccc(-c2ccccc2)cc1)CP(=O)(O)CCc1ccccc1]
(I)-n
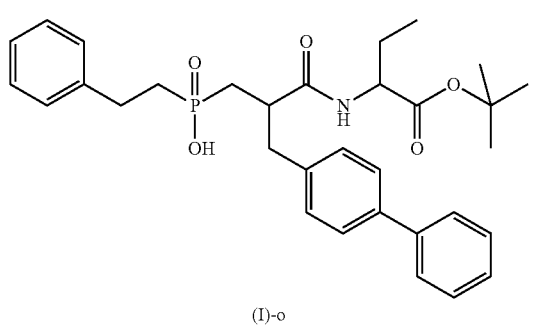
(I)-o
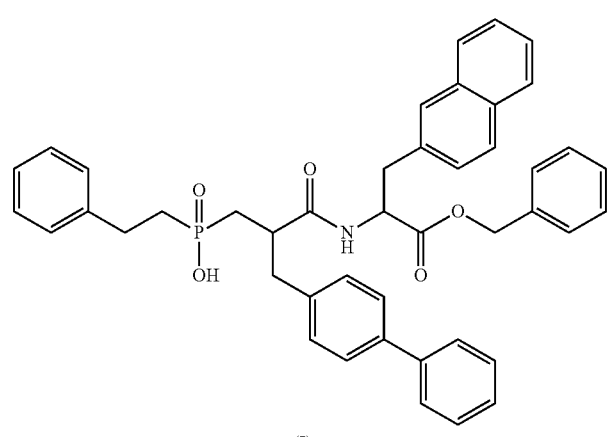
(I)-p
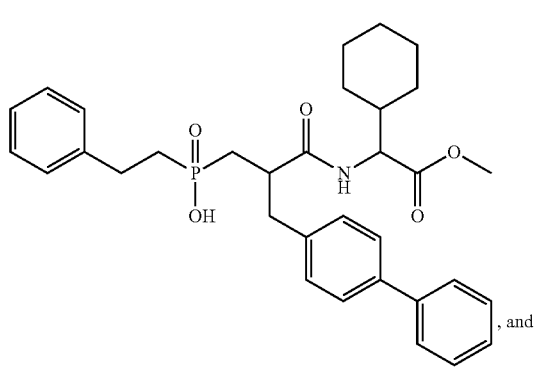 [SMILES: COC(=O)C(NC(=O)C(Cc1ccc(-c2ccccc2)cc1)CP(=O)(O)CCc1ccccc1)C1CCCCC1], and
(I)-q
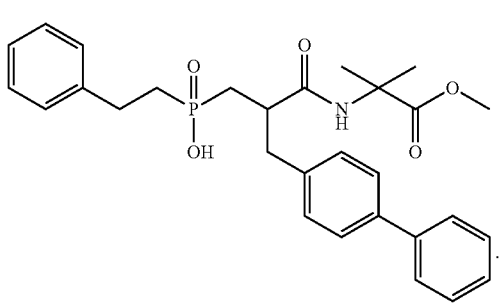 [SMILES: COC(=O)C(C)(C)NC(=O)C(Cc1ccc(-c2ccccc2)cc1)CP(=O)(O)CCc1ccccc1]
(I)-r 8. The compound according to claim 1, which is a compound selected from the group consisting of:

| | |
|---|---|
| ((S)-2-([1,1'-biphenyl]-4-ylmethyl)-3-(((S)-3-(benzo[b]thiophen-3-yl)-1-methoxy-1-oxopropan-2-yl)amino)-3-oxopropyl)(phenethyl)phosphinic acid | (I)-A |
| ((2S)-3-([1,1'-biphenyl]-4-yl)-2-((hydroxy(phenethyl)phosphoryl)methyl)propanoyl)-L-alloisoleucine | (I)-B |
| ((2S)-3-([1,1'-biphenyl]-4-yl)-2-((hydroxy(phenethyl)phosphoryl)methyl)propanoyl)-L-tryptophan salt with 2,2,2-trifluoroacetic acid (1:1) | (I)-C |
| ((R)-2-([1,1'-biphenyl]-4-ylmethyl)-3-(((S)-4-((tert-butoxycarbonyl)amino)-1-methoxy-1-oxobutan-2-yl)amino)-3-oxopropyl)(phenethyl)phosphinic acid | (I)-D |
| ((S)-2-([1,1'-biphenyl]-4-ylmethyl)-3-(((S)-1-(tert-butoxy)-4-methyl-1-oxopentan-2-yl)amino)-3-oxopropyl)(phenethyl)phosphinic acid | (I)-F |
| ((R)-2-([1,1'-biphenyl]-4-ylmethyl)-3-(((S)-1-(benzyloxy)-3-(naphthalen-2-yl)-1-oxopropan-2-yl)amino)-3-oxopropyl)(phenethyl)phosphinic acid | (I)-G |
| ((S)-2-([1,1'-biphenyl]-4-ylmethyl)-3-(((S)-1-methoxy-1-oxohexan-2-yl)amino)-3-oxopropyl)(phenethyl)phosphinic acid | (I)-H |
| ((2R)-3-([1,1'-biphenyl]-4-yl)-2-((hydroxy(phenethyl)phosphoryl)methyl)propanoyl)-L-asparagine | (I)-I |
| ((2S)-3-([1,1'-biphenyl]-4-yl)-2-((hydroxy(phenethyl)phosphoryl)methyl)propanoyl)-L-alanine | (I)-J |
| ((2R)-3-([1,1'-biphenyl]-4-yl)-2-((hydroxy(phenethyl)phosphoryl)methyl)propanoyl)-L-tryptophan compound with 2,2,2-trifluoroacetic acid (1:1) | (I)-K |
| 4-(3-([1,1'-biphenyl]-4-yl)-2-((hydroxy(phenethyl)phosphoryl)methyl)propanamido)butyric acid | (I)-L |
| (2S)-2-((2R)-3-([1,1'-biphenyl]-4-yl)-2-((hydroxy(phenethyl)phosphoryl)methyl)propanamido)-3-(benzo[b]thiophen-3-yl)propanoic acid | (I)-M |
| (2S)-2-((2R)-3-([1,1'-biphenyl]-4-yl)-2-((hydroxy(phenethyl)phosphoryl)methyl)propanamido)hexanoic acid | (I)-N |
| ((2S)-3-([1,1'-biphenyl]-4-yl)-2-((hydroxy(phenethyl)phosphoryl)methyl)propanoyl)-L-asparagine | (I)-O |
| ((S)-2-([1,1'-biphenyl]-4-ylmethyl)-3-(((S)-1-(tert-butoxy)-1-oxobutan-2-yl)amino)-3-oxopropyl)(phenethyl)phosphinic acid | (I)-P |
| ((S)-2-([1,1'-biphenyl]-4-ylmethyl)-3-(((S)-1-(benzyloxy)-3-(naphthalen-2-yl)-1-oxopropan-2-yl)amino)-3-oxopropyl)(phenethyl)phosphinic acid | (I)-Q |
| (2-([1,1'-biphenyl]-4-ylmethyl)-3-(((S)-1-(tert-butoxy)-3-(1-(tert-butoxycarbonyl)-1H-indol-3-yl)-1-oxopropan-2-yl)amino)-3-oxopropyl)(phenethyl)phosphinic acid | (I)-R |
| ((S)-2-([1,1'-biphenyl]-4-ylmethyl)-3-(((S)-1-cyclohexyl-2-methoxy-2-oxoethyl)amino)-3-oxopropyl)(phenethyl)phosphinic acid | (I)-S |
| ((R)-2-([1,1'-biphenyl]-4-ylmethyl)-3-(((2S,3R)-1-(tert-butoxy)-3-methyl-1-oxopentan-2-yl)amino)-3-oxopropyl)(phenethyl)phosphinic acid | (I)-T |
| ((S)-2-([1,1'-biphenyl]-4-ylmethyl)-3-(((2S,3R)-1-(tert-butoxy)-3-methyl-1-oxopentan-2-yl)amino)-3-oxopropyl)(phenethyl)phosphinic acid, and | (I)-U |
| (2-([1,1'-biphenyl]-4-ylmethyl)-3-((1-methoxy-2-methyl-1-oxopropan-2-yl)amino)-3-oxopropyl)(phenethyl)phosphinic acid | (I)-V. |

9. A cosmetic composition comprising the compound of formula (I) according to claim 1 and a cosmetically acceptable carrier.

10. The cosmetic composition according to claim 9, wherein the compound of formula (I) is present in an amount of 0.00001 to 0.5 wt.-%, based on the total weight of the cosmetic composition.

11. A compound according to claim 4, wherein the amino acid side chain has a functional group which is substituted with a tert-butyloxycarbonyl (Boc) group.

* * * * *